United States Patent [19]

Coope et al.

[11] Patent Number: 5,268,003
[45] Date of Patent: Dec. 7, 1993

[54] STABLE AMIDO PEROXYCARBOXYLIC ACIDS FOR BLEACHING

[75] Inventors: Janet L. Coope, Cliffside Park; Robert W. Humphreys, Oradell, both of N.J.; Stephen A. Madison, Valley Cottage, N.Y.

[73] Assignee: Lever Brothers Company, Division of Conopco, Inc., New York, N.Y.

[21] Appl. No.: 860,849

[22] Filed: Mar. 31, 1992

[51] Int. Cl.$^5$ ............... C07C 409/24; C07C 409/28; C07C 409/30; D06L 3/02

[52] U.S. Cl. ............................. 8/111; 544/387; 562/2; 252/186.1; 252/186.42; 252/102; 252/95

[58] Field of Search ............. 252/186.1, 186.42, 102, 252/95; 8/111; 562/2; 544/387

[56] References Cited

U.S. PATENT DOCUMENTS

| | | | |
|---|---|---|---|
| 4,758,369 | 7/1988 | Dyroff et al. | 252/95 X |
| 4,634,551 | 1/1987 | Burns et al. | 8/111 X |
| 4,642,198 | 2/1987 | Humphreys et al. | 252/95 X |
| 4,686,063 | 8/1987 | Burns | 252/95 X |
| 4,822,510 | 4/1989 | Madison et al. | 252/95 |
| 4,992,194 | 2/1991 | Liberati et al. | 252/95 X |
| 5,041,546 | 8/1991 | Venturello et al. | 252/95 X |
| 5,061,807 | 10/1991 | Gethoffer et al. | 8/111 X |
| 5,098,598 | 3/1992 | Sankey et al. | 252/186.42 |
| 5,149,864 | 9/1992 | Gethoffer et al. | 562/2 |

FOREIGN PATENT DOCUMENTS 0349220 1/1990 European Pat. Off.
0435379 7/1991 European Pat. Off.
WO90/14336 11/1990 PCT Int'l Appl.

OTHER PUBLICATIONS

American Chemical Society, CA114(21):206571t (1991).

American Chemical Society, Registry Nos. 133725-72-1 and 133725-71-0 (1991).

Primary Examiner—W. J. Shine
Assistant Examiner—Douglas J. McGinty
Attorney, Agent, or Firm—Milton L. Honig

[57] ABSTRACT

An amido peroxyacid compound is provided having the formula:

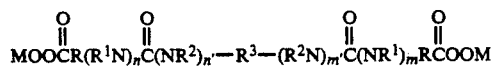

wherein

R is selected from the group consisting of $C_1$–$C_{12}$ alkylene, $C_5$–$C_{12}$ cycloalkylene, $C_6$–$C_{12}$ arylene and radical combinations thereof;

$R^1$ and $R^2$ are independently selected from the group consisting of H, $C_1$–$C_{16}$ alkyl and $C_6$–$C_{12}$ aryl radicals and a radical that can form a $C_3$–$C_{12}$ ring together with $R^3$ and both nitrogens;

$R^3$ is selected from the group consisting of $C_1$–$C_{12}$ alkylene, $C_5$–$C_{12}$ cycloalkylene and $C_6$–$C_{12}$ arylene radicals, and provided when $R^3$ is arylene and when n' and m' are each zero, R is other than $C_5$ alkylene;

n and n' each are an integer chosen such that the sum thereof is 1;

m and m' each are an integer chosen such that the sum thereof is 1; and

M is selected from the group consisting of H, alkali metal, alkaline earth metal, ammonium, alkanolammonium cations and radicals and combinations thereof.

The amido peroxyacid compound is useful for bleaching substrates such as stained laundry.

17 Claims, No Drawings

STABLE AMIDO PEROXYCARBOXYLIC ACIDS FOR BLEACHING

BACKGROUND OF THE INVENTION

1. Field of the Invention

The invention concerns novel amido peroxycarboxylic acids and their use as bleaches, especially in the cleaning of fabrics.

2. The Related Art

Organic peroxyacids have long been known for their excellent bleaching activity. For instance, U.S. Pat. No. 4,642,198 (Humphreys et al) describes a variety of water-insoluble organic peroxyacids intended for suspension in an aqueous, low pH liquid. The preferred peroxy material is 1,12-diperoxydodecanedioic acid (DPDA). Surfactants, both anionic and nonionic, were utilized as suspending agents for the peroxyacid particles. When formulated with 10% surfactant, the peracid had good stability under storage conditions. When the surfactant level of the formulation was increased to 22%, a level typical for a heavy-duty laundry detergent, the half-life of the DPDA decreased dramatically. For example, U.S. Pat. No. 4,992,194 (Liberti et al) reports that at 40° C. the half-life of DPDA was only 1 to 2 weeks in a pH 4–4.5 heavy-duty laundry liquid.

Another effective peracid is 4,4'-sulfonylbisperoxybenzoic acid (SBPB) reported in EP 0 267 175 (Dyroff et al) as possessing superior storage stability. U.S. Pat. No. 4,822,510 (Madison et al) demonstrates the increased stability of SBPB over DPDA in an aqueous liquid bleaching composition.

U.S. Pat. No. 4,634,551 (Burns et al) and U.S. Pat. No. 4,686,063 (Burns) describe peroxyacids having polar amide links along a hydrophobic backbone. These substances are stabilized with an exotherm control agent selected from boric acid and urea. Described in detail are a variety of n-acyl aminoperoxy acids and alkylamino oxoperoxy acids. All of the reported substances are mono-percarboxylic acids. A related patent, EP 0 349 220 (P&G), suggests use of a phosphate buffer solution and a pH between about 3.5 and 6 for improving storage stability of amido peroxyacids.

EP 0 349 940 (Hoechst AG) describes a series of imido peroxyacids, chief among which is N-phthaloylamino peroxycaproic acid (PAP). Suspension of imidoperoxycarboxylic acids in an aqueous system is achieved through use of sodium alkylbenzene sulfonate as reported in EP 0 435 379 (Akzo N.V.). Related technology in EP 0 347 724 (Ausimont) discloses heterocyclic peracids such as N-acyl-piperidine percarboxylic acids. WO 90/14336 (Interox) discloses 6,6'-terephthaldi(amidoperoxyhexanoic) acid and 6,6'-fumaryl bis(amidoperoxyhexanoic) acids.

Although many of the amido and imido peroxyacids have a quite dramatic bleaching activity, their stability in surfactant solutions remains a considerable problem. Clearly there is a need for new peracids specifically designed for heavy-duty laundry liquids. The materials also need to be physically stable in terms of thermal and shock sensitivity and in terms of storage stability.

In view of the problems of the art, it is an object of the present invention to provide new peroxycarboxylic acids with effective bleach activity.

Another object of the present invention is to provide peroxycarboxylic acids with superior storage stability.

Still another object of the present invention is to provide new peroxycarboxylic acids that, in addition to excellent activity, are also characterized by good storage stability when suspended in an aqueous medium.

A further object of the present invention is to provide a method of bleaching fabrics in a fully-formulated, heavy-duty laundry detergent composition through the use of new peroxycarboxylic acids.

These and other objects of the present invention will become more readily apparent through consideration of the following summary, detailed description and examples.

SUMMARY OF THE INVENTION

An amido peroxyacid compound is provided having the formula:

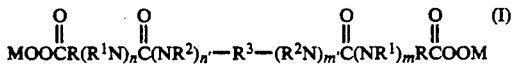

wherein:
R is selected from the group consisting of $C_1$–$C_{12}$ alkylene, $C_5$–$C_{12}$ cycloalkylene, $C_6$–$C_{12}$ arylene and radical combinations thereof;
$R^1$ and $R^2$ are independently selected from the group consisting of H, $C_1$–$C_{16}$ alkyl and $C_6$–$C_{12}$ aryl radicals and a radical that can form a $C_3$–$C_{12}$ ring together with $R^3$ and both nitrogens;
$R^3$ is selected from the group consisting of $C_1$–$C_{12}$ alkylene, $C_5$–$C_{12}$ cycloalkylene and $C_6$–$C_{12}$ arylene radicals, and provided when $R^3$ is arylene and when $n'$ and $m'$ are each zero, R is other than $C_5$ alkylene;
n and n' each are an integer chosen such that the sum thereof is 1;
m and m' each are an integer chosen such that the sum thereof is 1; and
M is selected from the group consisting of H, alkali metal, alkaline earth metal, ammonium, alkanolammonium cations and radicals and combinations thereof.

DETAILED DESCRIPTION

Now a new series of amido-type peroxycarboxylic acids has been found having the general formula:

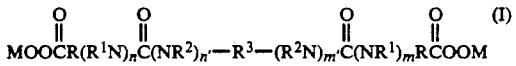

wherein:
R is selected from the group consisting of $C_1$–$C_{12}$ alkylene, $C_5$–$C_{12}$ cycloalkylene, $C_6$–$C_{12}$ arylene and radical combinations thereof;
$R^1$ and $R^2$ are independently selected from the group consisting of H, $C_1$–$C_{16}$ alkyl and $C_6$–$C_{12}$ aryl radicals and a radical that can form a $C_3$–$C_{12}$ ring together with $R^3$ and both nitrogens;
$R^3$ is selected from the group consisting of $C_1$–$C_{12}$ alkylene, $C_5$–$C_{12}$ cycloalkylene and $C_6$–$C_{12}$ arylene radicals, and provided when $R^3$ is arylene and when $n'$ and $m'$ are each zero, R is other than $C_5$ alkylene;
n and n' each are an integer chosen such that the sum thereof is 1;
m and m' each are an integer chosen such that the sum thereof is 1; and
M is selected from the group consisting of H, alkali metal, alkaline earth metal, ammonium, alkanolammonium cations and radicals and combinations thereof.

Within the general formula there are two subcategories of structures which are particularly advantageous. These substructures are as follows:

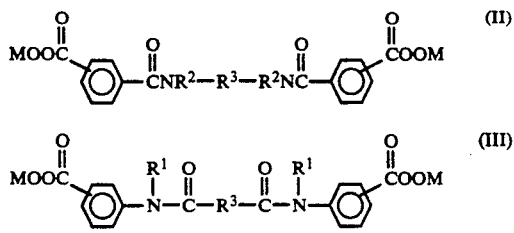

wherein:

$R^1$, $R^2$ and $R^3$ are defined in the same manner as that for formula I.

Particularly preferred compounds representing substructure (II) are the following:

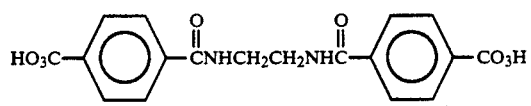

PCBED

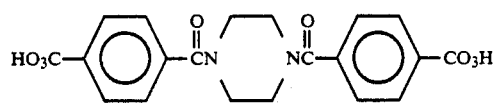

PCBPIP

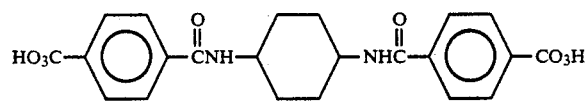

PCBHEX

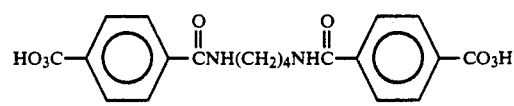

PCBBD

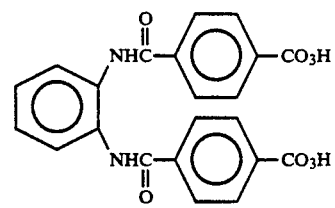

1,2—PCBPD

A particularly preferred compound representative of substructure (III) is as follows:

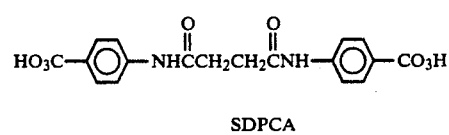

SDPCA

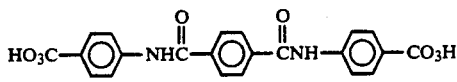

DPCAT

Synthesis of compounds according to the present invention can be accomplished through the condensation of difunctional amines and acids to form diacids or diesters linked by diamide moieties. Using this chemistry, there have been condensed a variety of diamines with two equivalents of the mono-acid chloride mono-ester of either terephthalic acid or adipic acid to provide some novel diamide diesters. Similarly, 4-aminobenzoic acid has been condensed with diacid chlorides to yield diamide diacids. Table I lists some of the combinations tested.

TABLE I

| Condensation Combinations Yielding Diamide Diesters | |
|---|---|
| Acid Derivative | Amine Derivative |
| 4-carbomethoxybenzoyl chloride | ethylenediamine |
| " | butanediamine |
| " | piperazine |
| " | trans-1,4-diaminocyclohexane |
| " | 1,4-phenylenediamine |
| " | 1,2-phenylenediamine |

TABLE I-continued

| Condensation Combinations Yielding Diamide Diesters | |
|---|---|
| Acid Derivative | Amine Derivative |
| carboethoxyadipoyl chloride | 1,4-phenylenediamine |
| " | ethylenediamine |
| succinoyl chloride | 4-aminobenzoic acid |
| terephthaloyl chloride | " |

Condensation of the diamines with the acid chlorides can be achieved by adding a toluene solution of the acid chloride dropwise to an aqueous solution of the diamine and excess potassium carbonate at room temperature. The resulting diamide precipitates from the biphasic reaction medium.

For purposes of this invention, the imido structure is not one encompassed herein.

A second method may be employed for those systems having special sensitivity to water. An anhydrous preparation is conducted where the amine and the acid chloride are dissolved in chloroform. Either pyridine or triethylamine can be utilized as a base for removing hydrogen chloride. This procedure is especially useful for compounds such as SDPCA and 1,2-PCBPD. For many of the amides, more than one method can successfully be employed in their preparation.

Conversion of the diamide diesters or diacids to the diperoxyacids may be accomplished using a standard procedure outlined by Swern et al described in Org. Synth., (1963), 43, 93–96 and in U.S. Pat. No. 3,180,886. The diesters or diacids, Which usually are completely soluble in methanesulfonic acid, may be treated with 6 to 9 molar equivalents of 70 or 90% hydrogen peroxide at room temperature for 3 to 5 hours. Conversion to the peracid from an aromatic carboxylic acid ester may range from 60 to 80% or higher; conversion of the aliphatic esters are usually even more successful being 90% or better.

When incorporated into a cleaning composition, the amido peroxyacids of the present invention will range in concentration from about 1 to about 40%, preferably from about 1.5 to about 15%, optimally between about 2 and about 5% by weight.

A detergent formulation containing a peroxyacid bleach system according to the invention will usually also contain surfactants and detergency builders. When in liquid form, the surfactants serve not only to clean but importantly function as a structuring system to suspend the water-insoluble amido peroxyacids in water or any other solvent carrier. For heavy-duty laundry liquids, it is also important to include a pH adjusting system and advantageously a deflocculating polymer.

The surface-active material may be naturally derived, such as soap or a synthetic material selected from anionic, nonionic, amphoteric, zwitterionic, cationic actives and mixtures thereof. Many suitable actives are commercially available and are fully described in the literature, for example in "Surface Active Agents and Detergents", Volumes I and II, by Schwartz, Perry and Berch. The total level of the surface-active material may range up to 50% by weight, preferably being from about 1% to about 40% by weight of the composition, most preferably 4 to 25%.

Synthetic anionic surface-actives are usually water-soluble alkali metal salts of organic sulfates and sulfonates having alkyl radicals containing from about 8 to about 22 carbon atoms, the term alkyl being used to include the alkyl portion of higher aryl radicals.

Examples of suitable synthetic anionic detergent compounds are sodium and ammonium alkyl sulfates, especially those obtained by sulfating higher ($C_8$–$C_{18}$) alcohols produced for example from tallow or coconut oil; sodium and ammonium alkyl ($C_9$–$C_{20}$) benzene sulfonates, particularly sodium linear secondary alkyl ($C_{10}$–$C_{15}$) benzene sulfonates; sodium alkyl glyceryl ether sulfates, especially those ethers of the higher alcohols derived from tallow coconut oil and synthetic alcohols derived from petroleum; sodium coconut oil fatty acid monoglyceride sulfates and sulfonates; sodium and ammonium salts of sulfuric acid esters of higher ($C_9$–$C_{18}$) fatty alcohol-alkylene oxide, particularly ethylene oxide reaction products; the reaction products of fatty acids such as coconut fatty acids esterified with isethionic acid and neutralized with sodium hydroxide; sodium and ammonium salts of fatty acid amides of methyl taurine; alkane monosulfonates such as those derived by reacting alpha-olefins ($C_8$–$C_{20}$) with sodium bisulfite and those derived by reacting paraffins with $SO_2$ and $Cl_2$ and then hydrolyzing with a base to produce a random sulfonate; sodium and ammonium $C_7$–$C_{12}$ dialkyl sulfosuccinates; and olefinic sulfonates, which term is used to describe the material made by reacting olefins, particularly $C_{10}$–$C_{20}$ alpha-olefins, with $SO_3$ and then neutralizing and hydrolyzing the reaction product. The preferred anionic detergent compounds are sodium ($C_{11}$–$C_{15}$) alkylbenzene sulfonates; sodium ($C_{16}$–$C_{18}$) alkyl sulfates and sodium ($C_{16}$–$C_{18}$) alkyl ether sulfates.

Examples of suitable nonionic surface-active compounds which may be used preferably together with the anionic surface active compounds, include in particular, the reaction products of alkylene oxides, usually ethylene oxide, with alkyl ($C_6$–$C_{22}$) phenols, generally 2–25 EO, i.e. 2–25 units of ethylene oxide per molecule; the condensation products of aliphatic ($C_8$–$C_{18}$) primary or secondary linear or branched alcohols with ethylene oxide, generally 2–30 EO, and products made by condensation of ethylene oxide with the reaction products of propylene oxide and ethylene diamine. Other so-called nonionic surface-actives include alkyl polyglycosides, long chain tertiary amine oxides, long chain tertiary phosphine oxides and dialkyl sulphoxides.

Amounts of amphoteric or zwitterionic surface-active compounds can also be used in the compositions of the invention but this is not normally desired owing to their relatively high cost. If any amphoteric or zwitterionic detergent compounds are used, it is generally in small amounts in compositions based on the much more commonly used synthetic anionic and nonionic actives.

The detergent compositions of the invention will normally also contain a detergency builder. Builder materials may be selected from (1) calcium sequestrant materials, (2) precipitating materials, (3) calcium ion-exchange materials and (4) mixtures thereof.

In particular, the compositions of the invention may contain any one of the organic or inorganic builder materials, such as sodium or potassium tripolyphosphate, sodium or potassium pyrophosphate, sodium or potassium orthophosphate, sodium carbonate, the sodium salt of nitrilotriacetic acid, sodium citrate, carboxymethylmalonate, carboxymethyloxysuccinate, tartrate mono- and di-succinates, oxydisuccinate, crystalline or amorphous aluminosilicates and mixtures thereof.

Polycarboxylic homo- and copolymers may also be included as builders and to function as powder structurants or processing aids. Particularly preferred are polyacrylic acid (available under the trademark Acrysol from the Rohm and Haas Company) and acrylic-maleic acid copolymers (available under the trademark Sokalan from the BASF Corporation) and alkali metal or other salts thereof.

These builder materials may be present at a level of, for example, from 1 to 80% by weight, preferably from 10 to 60% by weight.

Upon dispersal in a wash water, the initial amount of peroxyacid should range in amount to yield anywhere from about 0.05 to about 250 ppm active oxygen per liter of water, preferably between about 1 to 50 ppm. Surfactant should be present in the wash water from about 0.05 to 1.0 grams per liter, preferably from 0.15 to 0 20 grams per liter. When present, the builder amount will range from about 0.1 to 3.0 grams per liter.

For heavy-duty laundry detergent liquids, it is advantageous to employ a system to adjust pH, known as a pH "jump system". It is well-known that organic peroxyacid bleaches are most stable at low pH (3-6), whereas they are most effective as bleaches in moderately alkaline pH (7-9) solution. To achieve the required pH regimes, a pH jump system may be employed to keep the pH of the product low for peracid stability yet allow it to become moderately high in a wash water for bleaching and detergency efficacy. One such system is borax10H$_2$O/polyol. Borate ion and certain cis-1,2-polyols complex when concentrated to cause a reduction in pH. Upon dilution, the complex dissociates, liberating free borate to raise the pH. Examples of polyols which exhibit this complexing mechanism with borate include catechol, galactitol, fructose, sorbitol and pinacol. For economic reasons, sorbitol is the preferred polyol. To achieve the desired concentrate pH of less than 6, ratios greater than about 1:1 of polyol to borax are usually required. Therefore, the preferred ratio of polyol to borax should range anywhere from about 1:1 to about 10:1. Borate compounds such as boric acid, boric oxide, borax with sodium ortho- or pyroborate may also be suitable as the borate component.

Another advantageous component in the heavy-duty liquid laundry detergent compositions of this invention is a deflocculating polymer. Copolymers of hydrophilic and hydrophobic monomers usually are employed to form the deflocculating agent. Suitable polymers are obtained by copolymerizing maleic anhydride, acrylic or methacrylic acid or other hydrophilic monomers such as ethylene or styrene sulfonates and the like with similar monomers that have been functionalized with hydrophobic groups. These include the amides, esters, ethers of fatty alcohol or fatty alcohol ethoxylates. In addition to the fatty alcohols and ethoxylates, other hydrophobic groups, such as olefins or alkylaryl radicals, may be used. What is essential is that the copolymer have acceptable oxidation stability and that the copolymer have hydrophobic groups that interact with the lamellar droplets and hydrophilic groups of the structured liquid to prevent flocculation of these droplets and thereby, prevent physical instability and product separation. In practice, a copolymer of acrylic acid and lauryl methacrylate (M.W. 3800) has been found to be effective at levels of 0.5 to 1%. These materials are more fully described in U.S. Pat. No. 4,992,194 (Liberati et al) herein incorporated by reference.

Apart from the components already mentioned, the detergent compositions of the invention can contain any of the conventional additives in the amounts in which such materials are normally employed in detergent compositions. Examples of these additives include lather boosters such as alkanolamides, particularly the monoethanolamides derived from palmkernel fatty acids and coconut fatty acids, lather depressants such as alkyl phosphates and silicones, antiredeposition agents such as sodium carboxymethylcellulose and alkyl or substituted alkylcellulose ethers, other stabilizers such as ethylene diamine tetraacetic acid, fabric softening agents, inorganic salts such as sodium sulfate and usually present in very small amounts, fluorescent whitening agents, perfumes, enzymes such as proteases, cellulases, lipases and amylases, germicides and colorants.

The amido peroxyacids described herein are useful in a variety of cleaning products. These include laundry detergents, laundry bleaches, hard surface cleaners, toilet bowl cleaners, automatic dishwashing compositions and even denture cleaners. Peroxyacids of the present invention can be introduced in a variety of product forms including powders, on sheets or other substrates, in pouches, in tablets or in nonaqueous liquids such as liquid nonionic detergents.

The following examples will more fully illustrate the embodiments of this invention. All parts, percentages and proportions referred to herein and in the appended claims are by weight unless otherwise illustrated.

EXAMPLE 1

Monomethyl monopotassium terephthalate

A solution of 87.5% KOH (143 g, 2.24 moles) in 870 mL of methanol was added to ground dimethylterephthalate (434 g, 2.24 moles) in 2,420 ml toluene at room temperature over a period of 45 minutes. The reaction mixture was heated at 65° C. for three hours with stirring and was then allowed to cool to room temperature. The solids were filtered, washed with 3500 ml of warm toluene, and dried to yield 464.08 grams (95% yield) of a white solid. IR (nujol) 1735, 1600, 1550, 1410, 1290, 730 cm$^{-1}$.

N,N'-Di(4-carbomethoxybenzoyl)piperazine

Monomethyl monopotassium terephthalate (175.8 g, 0.8056 mol) was suspended in toluene (2000 mL) in a 5 L, 3-necked flask equipped with an overhead stirrer, a condenser, and an addition funnel. Thionyl chloride (58.76 mL, 0.8056 mol) was added dropwise to the rapidly stirred suspension and the mixture was heated at 67° C. for three hours. After stirring overnight at rt, the reaction was filtered on a Buchner funnel through a bed of celite and the filtrate containing 4-carbomethoxybenzoyl chloride was retained. At this point the acid chloride can be isolated by addition of an equal volume of diethyl ether, filtration of the potassium chloride by-product and removal of the solvent in vacuo. For most procedures the toluene solution is used directly.

In a 5 L Morton flask, potassium carbonate (266.2 g, 1.61 mol) and piperazine (34.69 g, 0.4027 mol) were dissolved in 1000 mL of water. The toluene solution of 4-carbomethoxybenzoyl chloride was added dropwise while the internal reaction temperature was maintained at 25° C. The mixture was stirred overnight, filtered and washed with toluene, water, 1N HCl and water to provide 127 g (77%) of N,N'-di(4-carbomethoxybenzoyl)-piperazine as a white solid mp. of 234°-237° C.

$^1$H NMR (200 MHz, CDCl$_3$/CD$_3$COCD$_3$) δ7.48-8.11 (8H, m), 3.93 (6H, S), 3.81 (4H, br s), 3.56 (4H, br S); $^{13}$C NMR (CDCl$_3$/CD$_3$COCD$_3$) δ169.51, 166.05, 139.19, 131.50, 129.89, 126.98, 52.31, 43.80, 41.10; IR (nujol) 2920, 2840, 1720, 1620, 1605, 1455, 1430, 1370, 1360, 1275, 1260, 1100, 1000 cm$^{-1}$; low res. MS (CI, isobutane) 411 (MH+).

N,N'-Di(4-percarboxybenzoyl)piperazine (PCBPIP)

N,N'-di(4-carboxybenzoyl)piperazine (4.07 g, 0.0099 mol) was dissolved in methanesulfonic acid (14 mL) and was treated with hydrogen peroxide (3.37 mL of a 70% solution, 0.0891 mol) at 0° C. The mixture was stirred at room temperature for 5 hours, then poured onto ice-water. The solids were collected on a Buchner funnel, washed with water until the pH was 5, then allowed to air dry overnight. Yield 3.91 g (95%) of a white powder; m.p. 268 (dec). Iodometric tritration indicated 65% peracid. IR (nujol) 3100 (hydroxyl), 1760 (peracid carbonyl) cm$^{-1}$.

EXAMPLE 2

N,N'-Di(4-Carbomethoxybenzoyl)ethylenediamine

Prepared using the procedure described for N,N'-di(-carbomethoxybenzoyl)piperazine and substituting ethylenediamine (26.9 mL, 0.4028 mol) for piperazine and using 400 mL of water instead of 1000 mL. Yield 88.6 g (57%); mp. 297°–299° C.; $^1$H NMR (200 MHZ, DMSO-d$_6$) δ8.82 (2 H, br s), 8.06–7.94 (8 H, m), 3.88 (6 H, s), 3.47 (4 H, s); IR (nujol) 3300, 1730, 1640, 1550 cm$^{-1}$.

N,N'-Di(4-Percarboxybenzoyl)ethylenediamine (PCBED)

N,N'-Di(4-carbomethoxybenzoyl)ethylenediamine (5.0 g, 0.0129 mol) was dissolved in 30 mL of methanesulfonic acid and treated with hydrogen peroxide (4.4 mL of a 70% solution) at 0° C. The mixture was allowed to warm to room temperature and was stirred for 5 hours. It was poured onto ice and saturated ammonium sulfate, the solids were filtered and washed with water to a pH of 5. The activity was 78% by iodometric titration.

EXAMPLE 3

N,N'-Di(4-carbomethoxybenzoyl)-1,4-phenylenediamine

4-Carbomethoxybenzoyl chloride (9.32 g, 0.046 mol) in chloroform (95 mL) was added to 1,4-phenylenediamine (2.59 g, 0.023 mol) in triethylamine (4.81 mL, 0.035 mol) and chloroform (250 mL) at 4° C. The reaction was allowed to warm to room temperature overnight. The chloroform was removed in vacuo. The solid was poured onto cold 5% HCl, filtered and washed with dilute HCl. Recrystallization from DMF yielded 6.16 g (62%) of a pale yellow powder; mp >345° C. $^1$H NMR (DMSO-d$_6$) δ8.06 (8H, s), 7.74 (4H, s), 3.88 (6H, s); $^{13}$C NMR (H$_2$SO$_4$/CD$_3$COCD$_3$) (dec. to acid) δ205, 196, 169.77, 167.10, 132.56, 130.95, 128.16, 127.79, 127.03, 122.85, 119.82, 52.02; IR (nujol) 3330, 2900, 2840, 1720, 1640, 1550, 1455, 1410, 1375, 1280, 1190, 1110 cm$^{-1}$; low res. MS(CI, isobutane) 433 (MH+), 271, 257, 223.

N,N'-Di(4-percarboxybenzoyl)phenylenediamine (1,4-PCBPD)

N,N'-Di(4-carbomethoxybenzoyl)phenylenediamine (3.07 g, 0.0071 mol) was dissolved in methanesulfonic acid (40 mL) and treated with hydrogen peroxide (2.42 mL of a 70% solution, 0.0639 mol) at room temperature. After stirring at room temperature for 6 hours, the reaction was kept at 3° C. for 12 hours. The mixture was poured onto saturated ammonium sulfate solution and ice, then isolated as before to yield 1.85 g (59%) of an orange powder; mp>315° C. Iodometric titration indicated 60% peracid. IR (nujol) 3230 (hydroxyl), 1755 (peracid carbonyl) cm$^{-1}$.

EXAMPLE 4

N,N'-Di(4-carbomethoxybenzoyl)-1,4-diaminocyclohexane

4-Carbomethoxybenzoyl chloride (9.057 g, 0.0456 mol) was dissolved in chloroform (180 mL) in a 500 mL 3-necked flask equipped with a mechanical stirrer and an addition funnel. To this solution was added trans-1,4-diaminocyclohexane (2.60 g, 0.0228 mol), triethylamine (7.5 mL, 0.0535 mol) and chloroform (80 mL) at 0° C. over a period of 30 minutes. The reaction was stirred for 2.5 hours and the product filtered from the chloroform. The wet solid was washed with 10% HCl and saturated aqueous NaCl. The product was dissolved in concentrated sulfuric acid at 0° C. and then crashed out from ice water to give a white powder in about 80% yield; m.p. >350° C. $^1$H NMR (200 MHz, D$_2$SO$_4$) δ8.30–7.94 (8H, m), 4.27–4.37 (8H, m), 2.34–1.80 (8H, br m), $^{13}$C NMR (200 MHz, H$_2$SO$_4$/CD$_3$COCD$_3$) δ170.92, 132.32, 129.92, 129.25, 127.61, 55.04, 51.83, 24.07; IR (nujol) 3295, 2920, 2850, 1720, 1630, 1530, 1460, 1375, 1285 cm$^{-1}$.

N,N'-Di(4-percarboxybenzoyl)-1,4-diaminocyclohexane (PCBHEX)

N,N'-Di(4-carboxybenzoyl)-1,4-diaminocyclohexane (1.63 g, 0.0037 mol) was dissolved in methanesulfonic acid (10 mL) and treated with hydrogen peroxide (1.26 mL of 70% solution, 0.0333 mol) at room temperature. After 7 hours, the reaction was worked-up with ice water and dried in a vacuum oven at 25° C. to give 1.57 g (95%) of a white powder; m.p. >310° C. Iodometric titration indicated 79% peracid. $^1$H NMR (200 MHz, DMSO-d$_6$) δ 8.47–8.44 (m, ester), 8.03–7.91 (m, peracid and ester), 3.88 (s, ester), 3.79 (br s, ester and peracid), 1.94–1.91 (m, ester and peracid), 1.52–1.43 (m, ester and peracid; IR (nujol) 3295 (broad, hydroxyl), 1730 (peracid carbonyl) cm$^{-1}$.

EXAMPLE 5

Carboethoxyadipoyl Chloride

Adipic acid monoethyl ester (25.63 g, 0.147 mol) was combined with thionyl chloride (34.98 g, 0.293 mol) in a round-bottomed flask equipped with a condenser and heated at 37° C. for 3 hours. The condenser was replaced by a modified still head and excess thionyl chloride removed at 5mm Hg. The product (26.84 g, 95%) was distilled as a clear liquid (59° C./about 0.1 mm Hg). IR 3550, 3420, 2950, 2910, 2840, 1785, 1715, 1455, 1360, 1230, 1170, 1140, 1080, 1010, 940 cm$^{-1}$.

N,N'-Di(carboethoxyadipoyl)-1,4-phenylenediamine

Carboethoxyadipoyl chloride (13.74 g, .071 mol) in chloroform (40 mL) was added to 1,4-phenylenediamine (3.89 g, 0.036 mol) in chloroform (330 mL) and triethylamine (7.53 mL, 0.054 mol) at 4° C. The reaction medium was allowed to warm to room temperature over the course of 5 hours. Recrystallization from ethyl acetate gave 6.30 g (42%) of a white fluffy solid; m.p. 156°–60° C. $^1$H NMR (DMSO-d$_6$) δ9.81 (2H, s, NH), 7.49 (4H, s), 4.04 (4H, q), 1.57 (8H, m), 2.34 (8H, m), 1.18 (6H, t); $^{13}$C NMR δ173.65, 171.25, 134.38, 120.74, 60.39, 36.90, 33.98, 25.01, 24.42, 14.23; IR (nujol) 3290, 2920, 2840, 1720, 1645, 1540, 1455, 1370, 1290, 1255, 1170 cm$^{-1}$; low res MS(CI, isobutane) 421 (MH+).

N,N'-Di(percarboxyadipoyl)phenylenediamine (DPAPD)

N,N'-Di(carboethoxyadipoyl)-1,4-phenylenediamine (6.00 g, 0.0143 mol) was dissolved in methanesulfonic acid (21 mL) and was treated with hydrogen peroxide (4.87 mL of a 70% solution, 0.1287 mol) at room temperature. The product was isolated from ice water after 2 hours to give 4.97 g (88%) of a pale orange powder; m.p. 210–212 (dec). Iodometric titration indicated 87% peracid. $^1$H NMR (200 MHz, DMSO-d$_6$) δ11.97 (2H, br, s), 9.83 (2H, s) 7.49 (4H, m), 4.10 (trace, q, ester), 2.49–2.00 (8H, m), 1.57 (8H, br s), 1.17 trace, t, ester); IR (nujol) 3100 (hydroxy), 1750 (peracid carbonyl) cm$^{-1}$.

EXAMPLE 6

N,N'-Di(4-carbomethoxybenzoyl)-1,4-butanediamine

4-Carbomethoxybenzoyl chloride (19.07 g, 0.096 mol) was dissolved in toluene (380 mL) in a 3-necked, 1000 mL round-bottomed flask equipped with mechanical stirrer, thermometer, and addition funnel A solution of 1,4-butanediamine in water (80 mL) was added dropwise over a period of 40 minutes while the temperature of the reaction mixture was maintained at 25° C. by a water bath. A white solid formed immediately and the reaction mixture stirred for an additional 2 hours. The solid was collected on a frit and washed with toluene, water, 5% HCl, and water. Recrystallization from DMF gave white crystals which were dried in a vacuum oven at 60° C.; yield 17.91 g (90%); m.p. 260°–261° C. $^1$H NMR (200 MHz, DMSO-d$_6$) δ8.70 (2H, m), 8.05–7.93 (8H, m) 3.88 (6H, s) 3.34 (4H, s), 1.58 (4H, s); IR (nujol) 3300, 1720, 1625, 1530, 1275, 1105, 860, 730 cm$^{-1}$; low res. MS (CI, isobutane) 413 (MH+); $^{13}$C NMR (75 MHZ, DMSO-d$_6$) δ166.9, 165.7, 165.4, 165.2, 138.7, 131.6, 129.0, 127.5, 127.2, 52.3, 26.5.

N,N'-Di(4-percarboxybenzoyl)-1,4-butanediamine (PCBBD)

N,N'-Di(4-carbomethoxybenzoyl)-1,4-butanediamine (3.00 g, 0.007 mol) dissolved in methanesulfonic acid (25 mL) was treated with hydrogen peroxide (2.50 mL of a 70% solution, 0.066 mol) according to the aforedescribed method. After 5 hours at room temperature and 16 hours at 3° C., the peracid was precipitated over ice water, washed with water and dried to give 1.8 g (60%) of a white powder; m p. 180 (dec). Iodometric titration indicated 74% peracid, 5.7% a.o. (theory: 7.7% a.o.). IR (nujol) 3320–3100 (hydroxyl), 1745 (peracid carbonyl) cm$^{-1}$; $^1$H NMR (200 MHz, DMSO-d$_6$) δ8.65 (2H, m), 8.03–7.90 (8H, m), 3.87 (starting material, 7%), 3.29 (4H, s), 1.58 (4H, s).

EXAMPLE 7

N,N-Di(4-carbomethoxybenzoyl) 1,2-phenylenediamine

4-Carbomethoxybenzoyl chloride (18.5 g, 0.093 mol) was dissolved in chloroform (100 mL) under nitrogen and cooled to 0° C. A solution of 1,2-phenylenediamine (5.00 g, 0.046 mol) and triethylamine (12.8 mL, 0.092 mol) in chloroform (350 mL) was added dropwise. After 16 hours at room temperature, triethylammonium chloride was removed by filtration on a frit containing filter paper. The organic layer was washed with cold 5% HCl (3×200 mL), saturated NaCl solution (2×150 mL), and dried over magnesium sulfate. The product was isolated by removal of chloroform under reduced pressure Recrystallization from ethanol yielded 12.19 g (61%) of a white powder; m.p. 211°–216° C. $^1$H NMR (200 MHz, DMSO-d$_6$) δ10.24 (2H, s), 8.09–8.07 (8H, 2s), 7.69 (2H, s), 7.33 (2H, s), 3.90–3.88 (6H, 2s); $^{13}$C NMR (50 MHz, DMSO-d$_6$) δ165.29, 164.37, 138.13, 131.81, 130.94, 128.94, 127.69, 125.79, 125.79, 125.42, 52.08; IR (nujol) 3380, 3280, 1720, 1645, 1540, 1290, 1275, 1100 cm$^{-1}$; low res. MS (Cl, isobutane) 433 (MH+) 271, 165.

N,N'-Di(4-percarboxybenzoyl)-1,2-phenylenediamine (1,2-PCBPD)

N,N'-Di(4-carbomethoxybenzoyl)-1,2-phenylenediamine (2.75 g, 0.0064 mol) was dissolved in methanesulfonic acid (25 mL) and cooleo to 0° C. Hydrogen peroxide (1.57 mL of a 90% solution, 0.058 mol) was added dropwise. After 16 hours at room temperature, the reaction was worked-up as described above. Iodometric titration indicated 70% peracid, 5.2% a.o. (theory: 7.3% a.o.) IR (nujol) 3160 (hydroxyl), 1740 (peracid carbonyl) cm$^{-1}$; $^1$H NMR (200 MHz, DMSO-d$_6$) δ10.20 (2H, s), 8.09–8.07 (8H, 2s), 7.73–7.52 (2H, m), 7.39–7.22 (2H, m), 3.89 (ester about 7%); $^{13}$C NMR (50 MHz, DMSO-d$_6$) δ166.58, 164.76, 137.95, 133.37, 131.19, 129.30, 127.76, 126.01.

EXAMPLE 8

N,N'-Succinoyl-di(4-carbomethoxy)aniline

Succinyl chloride was distilled under reduced pressure prior to use. To a 1000 mL round-bottomed flask under nitrogen, methyl-4-aminobenzoate (20 g, 0.132 mol), pyridine (10.7 mL, 0.133 mol), and chloroform (250 mL) were combined and cooled to 0° C. A chloroform solution of succinoyl chloride (7.5 mL, 0.068 mol) was added dropwise. A lavender precipitate was observed upon addition. After 2 hours at room temperature the product was filtered on a frit, washed with 5% HCl (2×400 mL), then with water (600 mL) and then allowed to air dry on the frit. The product was recrystallized from DMF and dried in a vacuum oven at 60° C. to afford 16.09 g (62%) of white crystals; m.p. 284°–285° C. $^1$H NMR (200 MHz, DMSO-d$_6$) δ10.42 (2H, s), 7.96–7.74 (8H, s), 3.85 (6H, s), 2.75 (4H, s); IR (nujol) 3340, 3320, 1710, 1690, 1675, 1610, 1595, 1530, 1295, 1270, 1175, 1160, 1105, 770 cm$^{-1}$; low res. MS (CI, isobutane) 385 (MH+), 234, 152; $^{13}$C NMR (75 MHz, DMSO-d$_6$) δ170.9, 165.7, 143.6, 130.2, 123.6, 118.2, 51.7, 31.0.

N,N'-Succinoyl-di(4-percarboxy)aniline (SDPCA)

N,N'-Succinoyl-di(4-carbomethoxy)aniline (5.02 g, 0.013 mol) was dissolved in methanesulfonic acid (30 mL) and cooled to 0° C. Hydrogen peroxide (4.43 mL of a 70% solution, 0.117 mol) was added dropwise. After 6 hours at room temperature, the product was worked-up as usual to give a light tan powder; m.p. 201° C. Iodometric tritration indicated 72% peracid, 6.0% a.o. (theory: 8.2% a.o.). IR (nujol) 3200 (hydroxyl), 1750 (peracid carbonyl) cm$^{-1}$; $^1$H NMR (200 MHz, DMSO-d$_6$) δ10.37, 10.34 (2H each, s, one for peracid —OH, one for amide —NH), 7.92–7.68 (8H, m), 3.81 (s, ester), 2.72 (4H, s, ester and peracid).

EXAMPLE 9

N,N'-Di(carboethoxyadipoyl)ethylenediamine

Ethylenediamine (1.17 g, 0.0195 mol) in water (5 mL) was added dropwise to a solution of carboethoxyadipoyl chloride (2.5 g, 0.013 mol) in toluene (36 mL) at room temperature. After stirring for an additional 2.5 hours, the white solid was filtered, washed with toluene, water, 0.1N HCl and water and dried in a vacuum oven at 63° C. In an attempt to eliminate an impurity evident in the IR spectrum (3080 cm$^{-1}$), the material was taken up in toluene, the insolubles removed by filtration, and the toluene removed in vacuo to yield a white powder (0.31 g, 13%); m.p. 117°–120° C. (white residue remained after most melted) $^1$H NMR (200 MHz, DMSO-d$_6$) δ7.83 (2H, br s), 4.05 (4H, q) 3.37 (H$_2$O),3.07 (5H, br s), 2.28–2.02 (10H, br s), 1.49 (9H, br s), 1.18 (6H, t); relative to the ethoxy protons, the integration of peaks at 3.07 and 1.49 is high by one proton each, and at 2.28–2.02 by two protons; IR (nujol) 3300, 3080, 2920, 2850, 1725, 1640, 1550, 1460, 1375, 1270, 1245, 1180, 730 cm$^{-1}$.

Since the toluene purification did not eliminate the unidentified impurity, the method described for the preparation of N,N'-(4-carbomethoxybenzoyl)piperazine was used. Carboethoxyadipoyl chloride (1.0 g, 0.0052 mol) in chloroform (12 mL) was added dropwise to a solution of ethylenediamine (0.16 g, 0.0026 mol), triethylamine (0.54 mL, 0.0039 mol), and chloroform (5 mL) at 4° C. under nitrogen. The mixture was stirred for 5.5 hours and worked up as usual to give 0.60 g (62%) of a solid. This product was recrystallized from toluene to give 0.20 g (21%) of a white powder which still contained the impurity by IR and NMR; m.p. 120°–122° C. Recrystallization from ethyl acetate also did not eliminate the impurity. $^{13}$C NMR (200 MHz, CDCl$_3$/CD$_3$COCD$_3$) δ207.44, 173.87, 60.38, 40.07, 36.08, 33.90, 25.12, 24.39, 14.33, 14.25; low res. MS(Cl, isobutane) 373 (MH+).

N,N'-Di(percarboxyadipoyl)ethylenediamine

N,N'-Di(carboethoxyadipoyl)ethylenediamine (0.203 g, 0.00055 mol) was dissolved in methanesulfonic acid (1.4 mL) and treated with hydrogen peroxide (0.19 mL of a 70% solution, 0.00495 mol) at room temperature and stirred for 18 hours. The product, which was difficult to isolate from ice water, was a white flaky material (0.0088 g, 46%) which turned black <220° C. but did not melt before 350° C. Iodometric titration indicated 55% peracid. $^1$H NMR (200 MHz, DMSO-d$_6$) δ7.81 (br s, ester and peracid), 4.10 (q, ester), 3.06 (H$_2$O), 2.22 and 2.19 (m, ester and peracid), 1.48 (m, ester and peracid), 1.19 (t, ester). IR (nujol) 3200 (hydroxyl) 1755 (peracid carbonyl) cm$^{-1}$.

EXAMPLE 10

N,N'-Di(4-carboxyaniline)terephthalate

4-Aminobenzoic acid (2.1 eq, 14.11 g, .103 mol) and sodium carbonate (5 eq, 25.92g, .245 mol) were stirred rapidly in 4000 mL water. Ground terephthaloyl chloride was added portionwise at room temperature. After stirring for 72 hours, the solution was poured onto 10% HCl. The solids were collected by filtration and washed with water to give 16.6g (83% yield) of a white powder. An impurity in this product is N-(4-carboxybenzoyl)4-aminobenzoic acid, which is the monoaddition adduct (less than 3%). $^1$H NMR (200 MHz, DMSO-d$_6$) δ10.74 (2 H, s), 8.15–7.90 (12 H, m), 3.4 (2H, br s); IR (nujol) 3360, 1690, 1660, 1610 cm$^{-1}$.

N,N'-Di(4-Percarboxyaniline)terephthalate (DPCAT)

N,N'-Di(4-carboxyaniline)terephthalate (4.98 g, 0.012 mol) was suspended in 60 mL of methanesulfonic acid and treated with hydrogen peroxide (4.09 mL of a 70% solution, 0.108 mol). The mixture was heated at 30° C. for 4.5 hours, then isolated as usual. Activity 91%, 6.7% a.o. (theoretical 7.3% a.o.). IR (nujol) 3380, 3200, 1740, 1660, 1600 cm$^{-1}$.

EXAMPLE 11

The bleaching performance of the peracids was evaluated against common stains such as tea (BC-1) and ink. Typically the cotton test pieces (3"×4") were stained with the appropriate stain and washed in a Terg-o-tometer for 15 minutes at 40° C. in a 500 mL aqueous wash solution. Dosage of the peracid was 10 ppm active oxygen.

Stain bleaching was measured reflectometrically using a Colorgard System/05 Reflectometer. Bleaching was indicated by an increase in reflectance, reported as ΔΔR. In general a ΔΔR of one unit is perceivable in a paired comparison while ΔΔR of two units is perceivable monadically. In reporting the reflectance change, the change in reflectance caused by general detergency has been accounted for. Thus ΔΔR can actually be expressed as:

$$\Delta\Delta R = \Delta R \text{ peracid} + \text{detergent} - \Delta R \text{ detergent}$$

where ΔR is the reflectance difference of the stained fabric after and before washing.

BC-1 experiments were run in duplicate and the value shown is an average. In order to ensure that the solids were as finely dispersed as possible, one of the BC-1 experiments of each pair was usually conducted by predissolving the peracid in 1 ml of DMF; if this value was within 1 unit of the experiment using finely ground peracid, the values were averaged. In the case of 1,2-PCBPD, this value was significantly different, thus, the DMF value is shown in parenthesis in Table II.

Ink stain bleaching was measured as ΔB where the quantity ΔB is the change in the B-axis of the Hunter color scale. The ink stain is initially blue and loses color with bleaching thereby increasing the value of ΔB. Recorded ΔΔB values are ΔB values corrected for the cleaning accomplished by the detergent control.

TABLE II

Bleaching Results at 40° C., 10 ppm A.O., P-Surf base (1.5 g l$^{-1}$)

| PERACID | BC-1 ΔΔR | | | INK ΔΔB |
|---|---|---|---|---|
| | pH 8 | pH 9 | pH 10 | pH 9 |
| PCBBD | 9.5 | 9.4 | 6.0 | 28.9 |
| 1,2-PCBPD | 4.4 (8.1) | 4.1 (6.5) | 3.9 | 24.9 |
| SDPCA | 2.7 | 3.3 | 5.0 | 16.8 |
| PCBED | 10.6 | 9.0 | 5.9 | 19.1 |
| DPAPD | 7.1 | 6.7 | 4.0 | 8.0 |
| PCBPIP | 3.0 | 2.9 | 3.1 | 9.7 |
| PCBHEX | 0.9 | 2.1 | 3.1 | 4.2 |
| DPCAT | 1.6 | 1.5 | 2.3 | 3.1 |

EXAMPLE 12

Differential Scanning Calorimetry (DSC)

A good indicator of the thermal sensitivity of the new peracids is their response to rapid heating. Table III contains data obtained from DSC analysis. The instrument used was a Dupont DSC with a 2910 cell base and 2100 thermal analyst. Samples of approximately 1 mg were acurately weighed into coated aluminum pans which were then hermetically sealed. After equilibration to 30° C., the samples were heated at a rate of 5° C./minute.

TABLE III

| Sample | Onset of Self-Heating (°C.) | Energy Released* Cal g⁻¹ | Kcal mol⁻¹ | MP (°C.) |
|---|---|---|---|---|
| PAP | 87 | 118 | 33 | 92 |
| DPDA | 96 | 366 | 96 | 96–99 |
| 1,2-PCBPD | 130 | 238 | 104 | |
| DPAPD | 137 | 291 | 115 | 210 (dec) |
| DPCAT | 140 | 277 | 121 | |
| SDPCA | 150 | 317 | 123 | |
| PCBPIP | 160 | 326 | 135 | 268 (dec) |
| PCBHEX | 175 | 246 | 109 | >310 |
| PCBED | 174 | 294 | 114 | 178 (dec) |
| SBPB | 178 | 354 | 120 | >290 |

*Corrected to 100% peracid content. Error is 5% or less.

All of the new peracids have onset temperatures in excess of 130° C. These high onset temperatures indicate good thermal stability and are desirable for the purposes of this invention. For purposes of the present invention it is advantageous for the peracid to have an onset temperature of at least 100° C., preferably from about 100° to 400° C., more preferably from 120° to 250° C., optimally between about 120° C. and 200° C.

EXAMPLE 13

Peracid Stability in a Heavy-Duty Liquid

The formulation used for this study contained 35% surface-actives and had a pH of 4.5 which was obtained with a borax/sorbitol pH jump system. The peracid was dosed to give 5 ppm A.O. in the wash (approximately 2 wt. % in the formulation). The formulations were stored at 40° C. and aliquots were removed periodically and titrated for the percent of remaining peracid.

TABLE IV

| Peracid Stability in a Heavy Duty Liquid | |
|---|---|
| Peracid | t½ at 40° C. (days) |
| PCBPIP | 79 |
| DPCAT | 65 |
| SDPCA | 43 |
| PCBED | 34 |
| 1,2-PCBPD | 33 |
| DPAPD | 32 |
| PCBBD | 15 |
| SBPB | 11 |
| DPDA | 5 |
| PAP | 3 |

All the new peracids were found more stable than DPDA and PAP in the heavy-duty liquid. Five of these had half-lives of greater than 30 days. PCBPIP had a noteworthy 79-day half-life at 40° C.

For the purposes of the present invention, it is advantageous to achieve a peroxide stability half-life at 40° C. of at least 10 days, preferably at least 15 days, more preferably at least 30 days, and optimally beyond 50 days.

The foregoing description and examples illustrate selected embodiments of the present invention. In light thereof, various modifications will be suggested to one skilled in the art, all of which are within the spirit and purview of this invention.

What is claimed is:

1. An amido peroxyacid compound having the formula

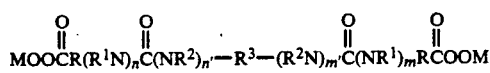

wherein:
R is selected from the group consisting of $C_1$–$C_{12}$ alkylene, $C_5$–$C_{12}$ cycloalkylene, $C_6$–$C_{12}$ arylene and radical combinations thereof;
$R^1$ and $R^2$ are independently selected from the group consisting of H, $C_1$–$C_{16}$ alkyl and $C_6$–$C_{12}$ aryl radicals and a radical that together with $R^3$ and both nitrogens forms a piperazine ring;
$R^3$ is selected from the group consisting of $C_1$–$C_{12}$ alkylene, $C_5$–$C_{12}$ cycloalkylene and $C_6$–$C_{12}$ arylene radicals, and provided when $R^3$ is arylene and when n' and m' are each zero, R is other than $C_5$ alkylene;
n and n' each are an integer chosen such that the sum thereof is 1;
m and m' each are an integer chosen such that the sum thereof is 1; and
M is selected from the group consisting of H, alkali metal, alkaline earth metal, ammonium, alkanolammonium cations and combinations thereof.

2. A peroxyacid according to claim 1 which has a structure selected from the group consisting of:

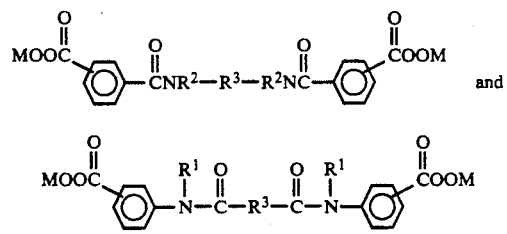

3. A peroxyacid according to claim 1 which is N,N'-di(4-percarboxybenzoyl)-1,4-butanediamine.
4. A peroxyacid according to claim 1 which is N,N'-di(4-percarboxybenzoyl)-1,2-phenylenediamine.
5. A peroxyacid according to claim 1 which is N,N'-succinoyl-di(4-percarboxy)aniline.
6. A peroxyacid according to claim 1 which is N,N'-di(4-percarboxybenzoyl)ethylenediamine.
7. A peroxyacid according to claim 1 which is N,N'-di(4-percarboxybenzoyl)piperazine.
8. A peroxyacid according to claim 1 which is N,N'-di(4-percarboxybenzoyl)-1,4-diaminocyclohexane.
9. A peroxyacid according to claim 1 which is N,N'-di(4-percarboxybenzoyl)-1,4-phenylenediamine.
10. A peroxyacid according to claim 1 which is N,N'-di(percarboxyadipoyl)-1,4-phenylenediamine.
11. A peroxyacid according to claim 1 which is N,N'-di(percarboxyadipoyl)ethylenediamine.
12. A peroxyacid according to claim 1 which is N,N'-Di(4-percarboxyaniline)terephthalate.
13. A peroxyacid according to claim 1 having a peroxide half-life at 40° C. of at least 10 days.
14. A peroxyacid according to claim 1 having a peroxide half-life at 40° C. of at least 30 days.
15. A peroxyacid according to claim 1 having a self-heating onset temperature of at least 100° C.

16. A peroxyacid according to claim 1 having a self-heating onset temperature between about 120° C. and 200° C.

17. A method for bleaching a substrate comprising applying to said substrate an effective amount to remove stain of an amido peroxyacid having the structure:

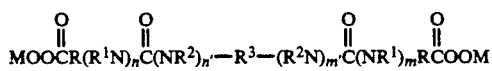

wherein:
R is selected from the group consisting of $C_1$–$C_{12}$ alkylene, $C_5$–$C_{12}$ cycloalkylene, $C_6$–$C_{12}$ arylene and radical combinations thereof;

$R^1$ and $R^2$ are independently selected from the group consisting of H, $C_1$–$C_{16}$ alkyl and $C_6$–$C_{12}$ aryl radicals and a radical that together with $R^3$ and both nitrogens forms a piperazine ring;

$R^3$ is selected from the group consisting of $C_1$–$C_{12}$ alkylene, $C_5$–$C_{12}$ cycloalkylene and $C_6$–$C_{12}$ arylene radicals, and provided when $R^3$ is arylene and when n' and m' are each zero, R is other than $C_5$ alkylene;

n and n' each are an integer chosen such that the sum thereof is 1;

m and m' each are an integer chosen such that the sum thereof is 1; and

M is selected from the group consisting of H, alkali metal, alkaline earth metal, ammonium, alkanolammonium cations and combinations thereof.

* * * * *